United States Patent [19]

Carignan et al.

[11] Patent Number: 5,147,386
[45] Date of Patent: Sep. 15, 1992

[54] SECURABLE PISTONING FINGER PROSTHESIS

[75] Inventors: Roger G. Carignan, Thousand Oaks; Gregory C. Rose, Ventura, both of Calif.

[73] Assignee: Techmedica, Inc., Camarillo, Calif.

[21] Appl. No.: 483,590

[22] Filed: Feb. 22, 1990

Related U.S. Application Data

[63] Continuation-in-part of Ser. No. 234,538, Aug. 22, 1988, abandoned.

[51] Int. Cl.⁵ .............................................. A61F 2/42
[52] U.S. Cl. ................................................... 623/21
[58] Field of Search ....................... 623/16, 18, 20, 21

[56] References Cited

U.S. PATENT DOCUMENTS

| | | | |
|---|---|---|---|
| 2,422,302 | 6/1947 | Horn | 623/20 |
| 2,696,817 | 12/1954 | Prevo | 623/20 |
| 2,719,522 | 10/1955 | Hudack | 623/20 |
| 3,506,982 | 5/1970 | Steffee | 623/20 |
| 3,651,521 | 3/1972 | Devas | 623/20 |
| 3,694,821 | 10/1972 | Moritz | 623/20 |
| 3,760,427 | 9/1973 | Schultz | 623/20 |
| 3,795,922 | 3/1974 | Herbert et al. | 623/20 |
| 3,990,118 | 11/1976 | Strickland et al. | 623/20 |
| 3,991,425 | 11/1976 | Martin | 623/20 |
| 4,003,096 | 1/1977 | Frey | 623/20 |
| 4,011,603 | 3/1977 | Steffee | 623/20 |
| 4,040,130 | 8/1977 | Laure | 623/20 |
| 4,059,854 | 11/1977 | Laure | 623/20 |
| 4,106,128 | 8/1978 | Greenwald | 623/20 |
| 4,131,957 | 1/1979 | Bokros | 623/20 |
| 4,158,893 | 6/1979 | Swanson | 623/20 |
| 4,180,871 | 6/1980 | Hamas | 623/20 |
| 4,231,121 | 11/1980 | Lewis | 623/20 |
| 4,276,660 | 7/1981 | Laure | 623/20 |
| 4,304,011 | 12/1981 | Whelan, III | 623/20 |
| 4,307,473 | 12/1981 | Weber | 623/20 |
| 4,352,212 | 10/1982 | Greene | 623/20 |

FOREIGN PATENT DOCUMENTS

| | | |
|---|---|---|
| 2839093 | 3/1980 | Fed. Rep. of Germany . |
| 3624525 | 7/1986 | Fed. Rep. of Germany . |
| 2575383 | 7/1986 | France . |

*Primary Examiner*—David J. Isabella
*Attorney, Agent, or Firm*—Cislo & Thomas

[57] ABSTRACT

A surgically implantable prosthetic phalangeal joint replacement device which allows twisting, pistoning, flexing, and lateral rotational movement made up of a ball joint held within a receptacle end defining a socket with enlarged or recessed sides, thereby allowing flexing and lateral rotational movement. Twisting and pistoning movement is achieved by a metacarpal body which interconnects the bones to be joined and rotatively and slidably connects to the ball joint. A pin can be used to securely retain the device together and allow the aforementioned range of motion.

23 Claims, 3 Drawing Sheets

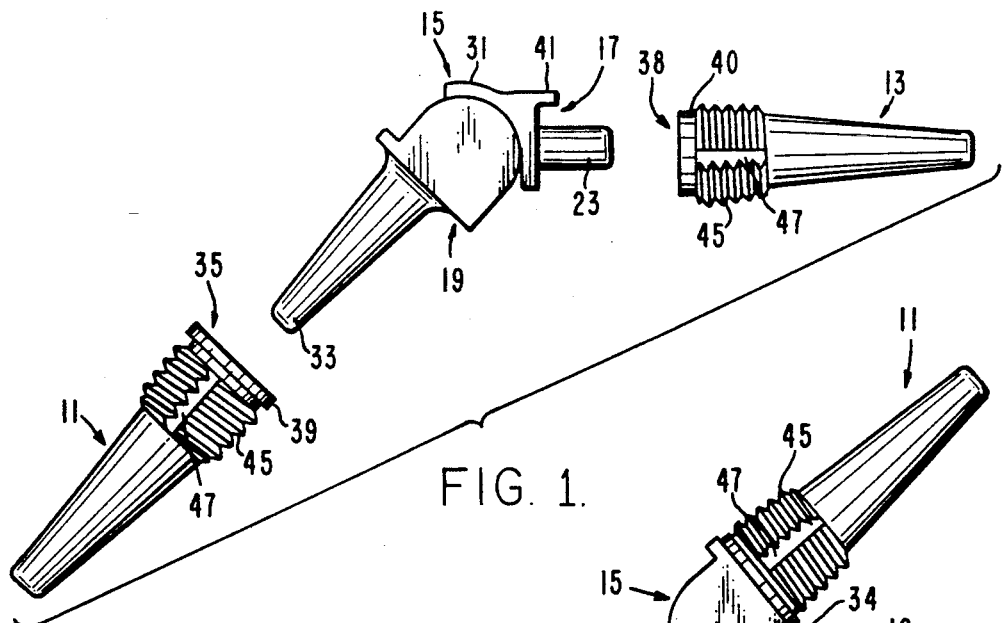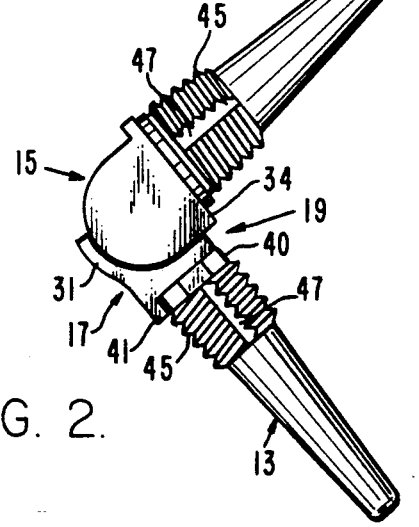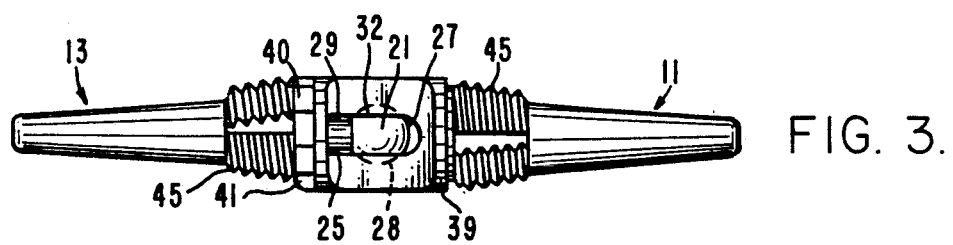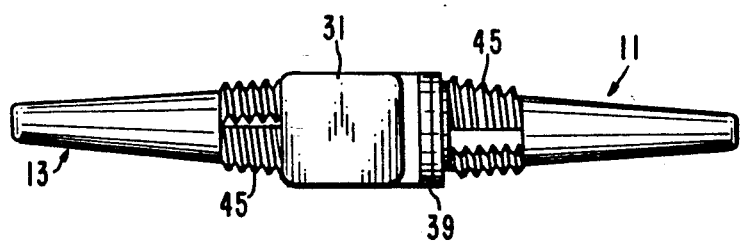

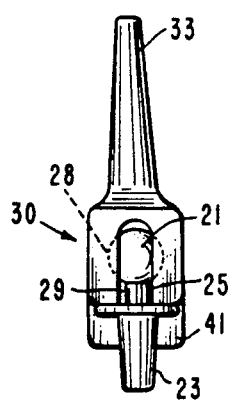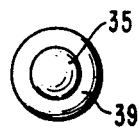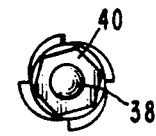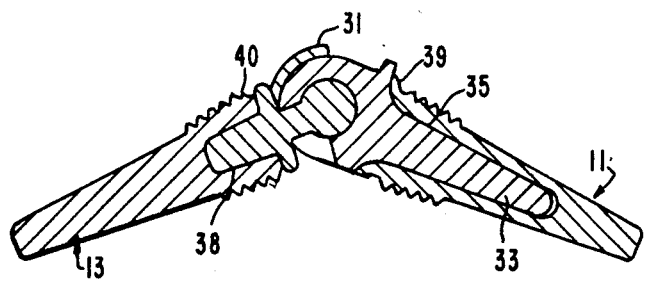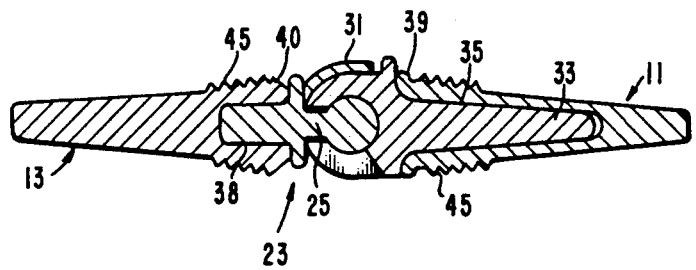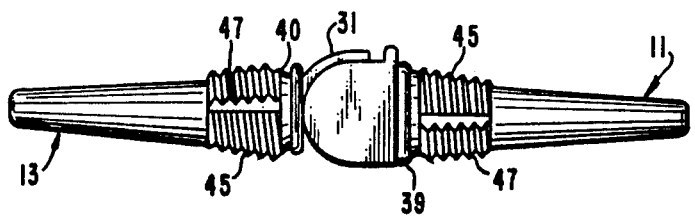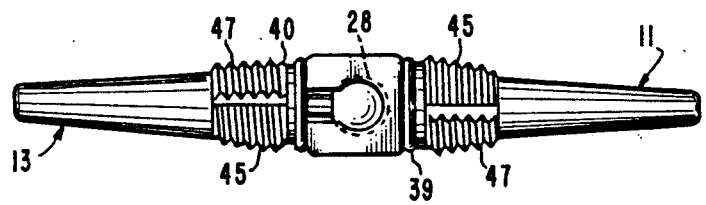

SECURABLE PISTONING FINGER PROSTHESIS

BACKGROUND OF THE INVENTION

This application is a continuation-in-part of an earlier filed application, Ser. No. 07/234,538 filed on Aug. 22, 1988 now abandoned.

This invention relates to surgically implantable prosthetic replacement devices for joints in the hand. Particularly, these devices are suitable for replacement of interphalangeal and metacarpal-phalangeal joints where such joints must be replaced due to accidents or diseases such as arthritis.

The replacement of certain finger joints has been known in the art and there are a number of patents which specifically address various structures to replace the joints within the finger, particularly between the phalangeal bones of the hand. These patents are U.S. Pat. No. 4,158,893, 4,059,854, 4,011,603, and 3,991,425. All of these patents allow a flexing motion and some lateral displacement of varying amounts.

However, these synthetic joints do not always replicate the characteristics of a human phalangeal joint. Particularly, the human phalangeal joint has the ability to flex in one plane just as one may curl his finger. The human joint can endure lateral movement and twisting to a slight degree. Additionally, a form of longitudinal play is possible along the length of the phalangeal joint. These four degrees of motion have been difficult to achieve in a synthetic joint which is durable, easily assembled, modular in approach so that an optimal bone-to-implant interface can be achieved, easily put into the human body, and which best replicates the joint that it replaces.

There is a great need in the prosthetic industry for phalangeal replacement joints, as well as other joints, which can achieve all of the desirable attributes articulated above. A phalangeal or other joint prosthesis should ideally incorporate these attributes.

The features identified above as being desired for phalangeal and other prostheses are all provided by the present invention.

SUMMARY OF THE INVENTION

The present invention is directed to an improved phalangeal prosthesis that best replicates the various movements available in a human phalangeal or other joint. The invention is simple in construction, modular, relatively easy to manufacture, easy to implant and reasonably durable.

More specifically, the prosthesis of the invention, for phalangeal joint replacement between proximal and distal phalangeal bones or between a distal phalangeal bone and a metacarpal bone is made up of three basic elements. A metacarpal body defines an axially located receiving chamber having interior tapered walls at one end, the other end being attached to the proximal phalangeal or metacarpal bone. A phalangeal body defines an axially located receiving chamber on one end, the other end being attached to the distal phalangeal bone.

Between the phalangeal body and the metacarpal body is a hinge means for joining the phalangeal body to the metacarpal body. The hinge means is of a construction which allows the twisting, flexing, pistoning, and laterally rotating (slight rotation perpendicular to a plane of joint flexion) between the phalangeal body and the metacarpal body which imitates a human metacarpal/phalangeal or phalangeal/phalangeal joint. This limited universal movement replicates the human finger.

The hinge means has a special construction which allows these four types of motion and is made up of three elements which allow these human-like movements. These three elements operatively associated are a hinge body, a hinge stem and a hinge retainer.

The hinge body has a receptacle end and a tapered extending end. The extending end operatively engages the receiving chamber of the metacarpal body such that the metacarpal body may ride on the extending end and allow twisting, flexing and pistoning movement. On the other end of the hinge body a receptacle end defines a socket for holding the hinge stem.

The hinge stem has a ball end which is received within the socket and an extending end which operatively engages the receiving chamber of the phalangeal body such that the phalangeal body is friction-fitted to the extending end of the hinge stem.

A hinge retainer is positioned and held midway along the hinge stem. The hinge retainer has a surface contoured to the exterior of the receptacle end of the hinge body and retains the ball end of the hinge stem within the socket of the hinge body.

The socket of the receptacle end of the hinge body has chamfered or recessed sides within the socket allowing a predetermined amount of lateral rotational movement of the ball end of the hinge stem. The ball end is captively, but loosely received for allowing limited universal movement.

The hinge stem further comprises a neck between the ball end and the hinge retainer. The receptacle end further defines a radially located slot adjacent to the socket sized to allow movement of the neck through the slot to prevent the ball end of the hinge stem from moving out of the socket. The radial slot may also have externally chamfered walls to provide a specific degree of lateral rotation between the hinge body and the hinge stem.

In an alternative embodiment, the hinge retainer is eliminated and a pin is centrally located through the ball end of the hinge stem which has a length sufficient to engage predefined recesses or slots within the socket of the hinge body. The recesses or slots can be positioned to allow rotational flexion simulating the replaced joint. Also, the hinge stem has a star-shaped collar which can be engaged by extending tabs of the phalangeal body to prevent relative rotation thereof. Finally, both the phalangeal body and the metacarpal body have slots to allow the bodies to be screwed into their respective bones using a tabbed tool.

In this embodiment, the positioning of the extending end of the hinge body relative to the extending end of the hinge stem may be axially offset in a fully extended position to provide increased mechanical advantage for weakened soft tissue found in diseased or injured fingers. This offset can be incorporated in the first embodiment as well.

Other aspects and advantages of the present invention will become apparent in the following description of the preferred embodiments, taken in conjunction with the accompanying drawings, which illustrates, by way of example, the principles of the invention.

BRIEF DESCRIPTION OF THE DRAWINGS

FIG. 1 is an exploded side view of the prosthesis device of the present invention;

FIG. 2 is a side view of the prosthesis device illustrated in FIG. 1;

FIG. 3 is a bottom plan view of the prosthesis device of FIG. 1;

FIG. 4 is a top plan view of the prosthesis device of FIG. 1;

FIG. 5 is a bottom plan view of the prosthesis device of FIG. 1 with the phalangeal body and metacarpal body not present;

FIG. 5a is a distal end plan view of the metacarpal body;

FIG. 5b is a proximal end plan view of the phalangeal body;

FIG. 6 is an elevational cross-sectional view of the prosthesis device of FIG. 1 in a flexing position;

FIG. 7 is an elevational cross-sectional view of the prosthesis device in FIG. 1 in a fully extended position;

FIG. 8 is a plan side view of the prosthesis device in FIG. 1 in a fully extended position;

FIG. 9 is a plan bottom view of the prosthesis device in FIG. 1 in a fully extended position with recesses shown in phantom line;

DESCRIPTION OF THE PREFERRED EMBODIMENTS

Figure 10:
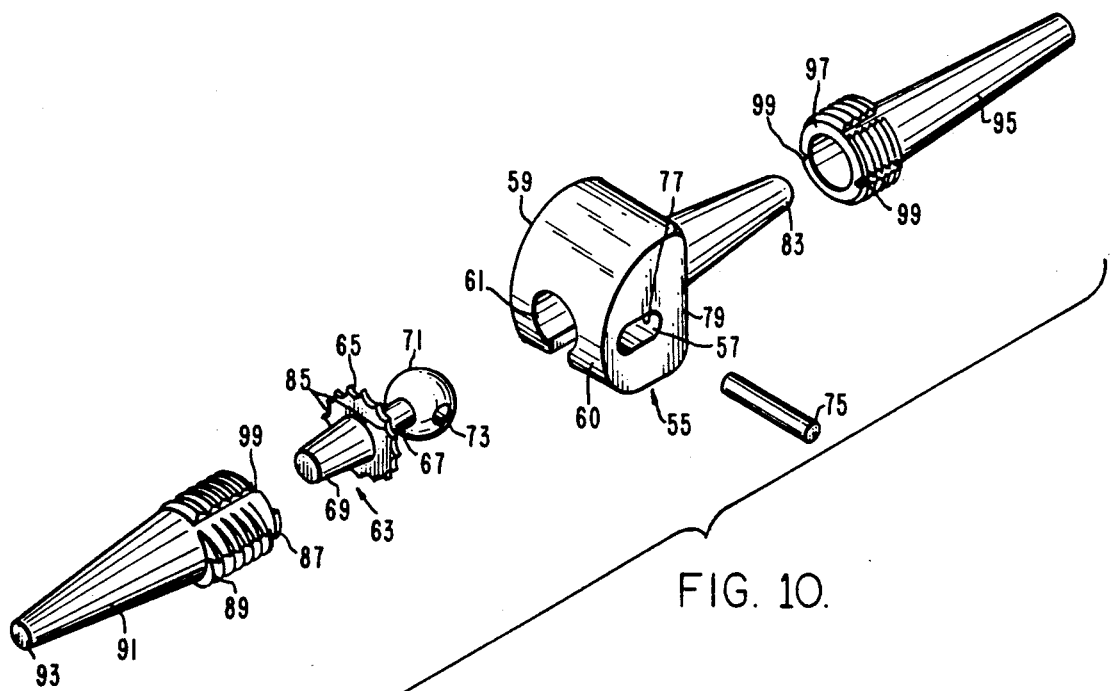
FIG. 10 is an exploded view of an alternative embodiment of the prosthesis of the present invention.

As shown in the drawings wherein like numerals represent like elements, particularly FIGS. 1, 2, 3, 4 and 5, the invention depicted is a prosthetic device primarily consisting of three operatively associated components: a metacarpal body 11, a phalangeal body 13, and a hinge member 15. All three components operate in cooperation to provide twisting, flexing, pistoning, and lateral motions simulating the human finger joint.

The hinge member 15 has a unique configuration which allows flexing and lateral movement. The hinge member 15 is made up of primarily two components. A hinge stem 17 operatively engages a hinge body 19 allowing both flexing and laterally movement. The hinge body 19 is integrally formed of a plastic material.

The hinge stem 17 has a ball end 21 having a spherical shape. The hinge stem's other end has a tapered extending end 23 designed to engage the phalangeal body 13 which can incorporate a friction fit taper-lock. Between the extending end 23 and the ball end 21 is a neck portion 25. The neck portion 25 has a lesser diameter than the diameter of the ball end 21 while the neck portion 25 may or may not have a diameter greater than the diameter of the extending end 23.

The ball end 21 of the hinge stem 17 is positioned within a socket 27 defined within the hinge body 19. The ball end 21 is positioned within the socket 27 so that the hinge stem 17 is so held by the hinge body 19 substantially restricting flexion motion to one plane. This is achieved by a slot 29 which runs transversely through the hinge body 19 along a locus measuring 95°. The length of the slot 29 restricts the rotation of movement of the hinge stem 17 within the hinge body 19 to approximately 95°. However, walls of the slot 29 may be externally chamfered to allow some slight universal movement of the hinge stem 17 within the socket 27.

The 95° movement is possible because the socket 27 of the hinge body 19 acts as a receptacle end 30 and the ball end 21 of the hinge stem 17 is held within the socket 27. The neck portion 25 extends through the slot 29 to the exterior of the hinge body 19. Therefore, the hinge stem 17 can rotate through the slot 29 which makes a 95° angle through the hinge body 19.

The rotation of the hinge stem 17 in relationship to the hinge body 19 can only occur along the length of the slot 29. This allows the flexing motion of the prosthesis as a finger can flex over approximately 90° of relative rotation.

The dimensions of the slot 29 are such that slight lateral rotation perpendicular to the direction of flexing is possible. Walls 28 (shown in phantom) of the socket 27 of the hinge body 19 are spherical and may be slightly enlarged to allow the ball end 21 of the hinge stem 17 to be loosely held. Also, exterior edges 32 along the radial slot 29 may be externally chamfered, recessed or tapered outwardly slightly about 10°. This tapering allows slight rotational or universal motion of approximately 10° to occur perpendicular to the flexing motion. This allows the finger limited universal movement.

One end of the slot 29 is wider having an almost circular shape for receiving the ball end 21 of the hinge stem 17. This widening of the slot allows that ball end 21 to be pushed into the socket 27 during assembly of the components. The socket 27 is of a softer, more flexible material which can be displaced when the harder ball end 21 is pushed into the socket 27. As a result, the ball end 21 is held within the socket 27 as the walls 28 of the socket 27 return to their original shape.

A hinge retainer 31 prevents the ball end 21 from popping out of the socket 27 during flexing. The hinge retainer 31 is positioned and held between the extending end 23 of hinge stem 17 and the neck portion 25. The hinge retainer 31 is a strip of metal having a curved shape contoured to the exterior of the receptacle end 30 of the hinge body 19. The hinge retainer 31 rides along the surface of the hinge body 19 during flexing motion when the hinge body 19 and hinge stem 17 rotate relative to each other. The hinge retainer 31 allows the flexing movement between the hinge body 19 and the hinge stem 17 while preventing the ball end 21 from popping out of the socket 27 in the receptacle end 30 of the hinge body 19.

The structural and functional relationships between the hinge body 19 and the hinge stem 17 allow the flexing and lateral rotational movement necessary in a phalangeal or metacarpal prosthesis.

Defining more fully the hinge body 19 best explains how the present invention achieves the twisting and pistoning motion or movement between the proximal phalangeal or metacarpal bone (not shown) and the hinge means 15.

The hinge body 19 has an extending end 33 which operatively engages the metacarpal body 11. The extending end 33 is tapered so that it narrows and is complementary shaped so that the extending end may fit or seat within the similarly tapered receiving chamber 35 axially located within the metacarpal body 11. The receiving chamber 35 is shown in FIG. 5A. However, there is sufficient space between the extending end 33 and the metacarpal body 11 within the receiving chamber 35 to allow a relative degree of flexing between the metacarpal body 11 and the extending end 33 when the metacarpal body 11 is distracted away from the extending end 33. When the extending end 33 is full seated within the receiving chamber 35, this relative degree of flexing cannot occur. Because the extending end 33 is complementarily tapered to the tapering of the receiving chamber 35, as distraction occurs, the hinge body 19 does not necessarily need to stay aligned with the metacarpal body 11. This is a substantial improvement over a cylindrical arrangement which would more readily transfer and magnify torsion to the prosthesis. Therefore, the tapered arrangement reduces the prospect of the metacarpal body 11 or phalangeal body 13 loosening once implanted. Thus, the metacarpal body 11 is not constrained to be in axial alignment with the hinge body 19, but instead can flex, except when the extending end 33 is fully seated within the receiving chamber 35.

When the prosthesis is properly installed, the metacarpal body 11 is secured and embedded within a cavity (not shown) provided in the distal phalangeal bone or metacarpal bone (not shown) to be so joined. The extending end 33 of the hinge body 1 is positioned within the receiving chamber 35 so that the metacarpal body 11 along with the proximal phalangeal or metacarpal bone may rotate and/or distract while still engaging the extending end 33 of the hinge body 19.

It is important for a prosthesis to allow these degrees of motion, especially in a metacarpal or phalangeal joint to reduce tensile forces which may be transferred across the joint connections. Without this articulation the phalangeal bone or metacarpal bone could pull away from the prosthesis causing damage to the connected bone and tissue.

Also, the twisting motion that is allowed is important. The metacarpal body 11 can radially twist relative to the extending end 33 of the hinge body 19. Likewise, the prosthesis is less likely to tear away from its implanted location under torque.

Finally, the ability of the extending end 33 of the hinge body 19 to distract from the receiving chamber 35 of the metacarpal body 11 and deflect axially prevents torsion in the plane perpendicular to the axis of the prosthesis.

The hinge body 19 between the receptacle end 30 and the extending end 33 has a flat surface 34 surrounding the base of the extending end. This flat surface 34 allows the widest end of the metacarpal body 11 to abut against it. The metacarpal body 11 has a circular lip 39 which surrounds the widest end of the metacarpal body 11. Thus, the lip 39 comes in contact with the flat surface 34 of the hinge body 19 when the proximal phalangeal or metacarpal bone (not shown) is pushed or compressed against the distal phalangeal bone (not shown) joined by the prosthetic joint.

The phalangeal body 13 can be similar to the metacarpal body/hinge body connection, and can engage the extending end 23 of the hinge stem 17, but does not piston. The connector may be of a taper-lock type.

As shown in FIG. 5B the phalangeal body 13 has a receiving chamber 38 on its widest end which is axially located to allow the complementing extending end 23 of the hinge stem 17 to fit within the receiving chamber 38 causing a friction-fit.

At the phalangeal body's widest end is a lip 40 having a hexagonal shape which can engage a tab 41 between the extending end 23 and the hinge retainer 31. The tab 41 can be an extension of the hinge retainer 31. The tab 41 may be located at a variety of places between the extending end 23 and the hinge retainer 31. The lip 40 and the tab 41 are of such a configuration so as to prevent the phalangeal body 13 from rotating on or relative to the extending end 23 of hinge stem 17.

Both the phalangeal body 13 and the metacarpal body 11 may have self-tapping threading 45 on their wider ends so that both can be positioned into their respective bones to be connected and rotatively implanted. Many lengths and different diameters assure the ability of a surgeon to achieve a tight fit between the prosthesis and the receiving bone of the instant invention. This allows the prosthesis to be connected at the end of the bones to be joined. However, threading may not be necessary as a contoured surface (not shown) may also serve to anchor the prosthesis to the bone to be joined.

Interrupting channels 47 allow the threading to be easily screwed into the bones to be joined, yet make for a secure joint. The bone to be joined grows in and around the channels preventing the phalangeal body 13 and the metacarpal body 11 from pulling free of their respective bones.

The phalangeal body 13 and metacarpal body 11 are made out of titanium or other durable implantable material which will not harmfully interact with the human body. The hinge stem 17 and hinge retainer 31 are made of an alloy of cobalt and chrome or some other implantable material that it will not interact harmfully with the human body, yet remain durable over many years.

The hinge body 19 is made out of a high-strength plastic such as ultra high molecular weight polyethylene which can flex to allow the ball end 21 of the hinge stem 17 to be pushed into the socket 27 of the hinge body 19.

Figure 11:
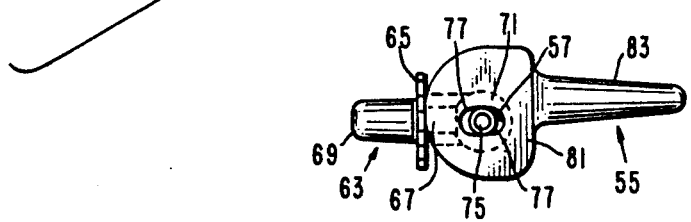
FIG. 11 is an elevational view of the alternative embodiment shown in FIG. 10 of the prosthesis of the present invention without the metacarpal body and phalangeal body, and showing portions of the hinge stem and interior walls of the socket in phantom line.

Finally, the extending end 33 of the hinge body 19 can be axially offset from the hinge stem 23 when the hinge member 15 is in a fully extended position as shown in FIGS. 3, 4, 7, 8, and 9 and more particularly shown in FIG. 11. This axial offset offers greater mechanical advantage offering better performance in view of the weakened soft tissue found in diseased or injured fingers.

Figure 12:
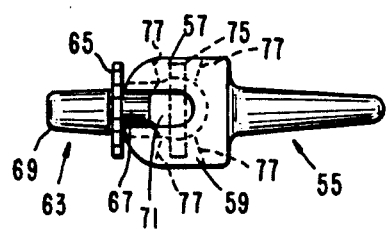
FIG. 12 is a bottom plan view of the alternative embodiment shown in FIGS. 10 and 11 of the prosthesis of the present invention without the metacarpal body and the phalangeal body, and showing portions of the hinge stem, interior walls of the socket, and the retaining pin in phantom line.

In an alternative embodiment as shown in FIGS. 10-12, the hinge retainer 31 as shown in FIGS. 1-9 can be eliminated, including the tab 41 and the lip 40 of the phalangeal body 13. As shown most particularly in FIG. 10, a modified hinge body 55 is similar to the hinge body 19 of the first embodiment, except slots 57 and 59 are transversely cut through a receptacle end 59 so as to communicate with a socket 61.

A modified hinge stem 63 has a star-shaped collar 65 separating a neck portion 67 an extending end 69. Associated with the neck portion 67 is a spherical ball element 71 which includes a centrally located bore 73 transversely cut therethrough perpendicular to a plane axial to the extending end 69 of the hinge stem 63.

The ball element 71 is associated with the modified hinge body 55 and is loosely and captively held within the socket 61. The bore 73 of the ball element 71 can be aligned with the slots 57 and 59 of the modified hinge body 55. A pin 75 is of a diameter so as to be insertable within the bore 73 of the ball element 71 and of a length greater than the diameter of the ball element 71, yet shorter than the distance between the exteriors of slots 57 and 59.

The pin 75 helps to retain the ball element 71 within the socket 61 of the modified hinge body 55. Also, the pin 75 restricts the movement of the ball element 71 relative to the modified hinge body 55 since the pin 75 can only move within the slots 57 and 59.

The slots 57 and 59 have outwardly tapered interior walls 77 (shown in phantom line in FIG. 12) opposite each other and positioned so as to allow the hinge stem 63 to rock or flex in a variety of different planes, including a plane perpendicular to a flat surface 79 surrounding a base 81 of the extending end 83 of the modified hinge body 55. This arrangement provides for controlled movement of the hinge stem 63 relative to the modified hinge body 55. By positioning the slots 57 and 59 and changing the tapering of the interior walls 77 and/or changing the width or length of the slots 57 and 59 relative to the pin 75, a greater or lesser degree of flexing or rocking can be accomplished.

Obviously, the pin 75 is insertable through the ball element 71 and extends a length so as to abut up against the interior walls 77 of the slots 57 and 59. The pin 75 can be friction fit or otherwise fastened within the bore 73 of the ball socket 71, once the ball element 71 is inserted within the socket 61.

The star-shaped collar 65 has a plurality of large serrations 85 which are radially spaced on its periphery and has a complementary shape to at least one tab or tabs 87 longitudinally extending from a second end 89 of a modified phalangeal body 91. A first end 93 of the phalangeal body is tapered and smooth for implantation purposes. The tabs 87 are of a shape and are aligned upon the second end 89 of the phalangeal body to engage the serrations 85 of the star-shaped collar 65. Thus, relative rotation between the hinge stem 63 and the phalangeal body 91 is not possible when so engaged. However, the hinge stem 63 and the phalangeal body 91 can be easily separated longitudinally. Although this is the preferred approach for preventing relative rotation between the phalangeal body 91 and the hinge stem 67, other approaches are possible.

In essence, the star-shaped collar 65 and the pin 75 of the second embodiment functionally replace the hinge retainer 31, and the tab 41 of the first embodiment.

A modified metacarpal body 95 has a second end 97 with exposed slots 99 which are engagable by a tool not shown. The tool such as a screwdriver or the like not shown can be used to rotationally screw the metacarpal body 95 into a bone upon implantation. Similarly, the second end 89 of the phalangeal body 91 can have the exposed slots 99 to allow the tool not shown to rotationally screw the phalangeal body 91 into a bone upon implantation.

With the exception of the above-described differences, the second embodiment of the invention is similar to the first embodiment of the invention which has been heretofore described and which description equally applies herein.

It should be appreciative from the foregoing description that the present invention provides an improved prosthetic for the replacement of metacarpal and phalangeal joints. The prosthesis allows for twisting, flexing, pistoning, universal flexing and lateral rotational movement, yet is simple in design and effective in holding a metacarpal or proximal phalangeal bone and distal phalangeal bone together. The joint is durable and allows the movements of a normal finger.

Although the present invention has been described in detail with reference only to the presently preferred embodiment, it will be appreciated by those of ordinary skill in the art that various modifications can be made without departing from the invention. Accordingly the invention is limited only by the following claims.

We claim:

1. A prosthesis device for phalangeal joint replacement between a proximal phalangeal or metacarpal bone and a distal phalangeal bone comprising:
   (a) an independent metacarpal body having a first end adapted for operative securement to human bone and a second end defining an axially oriented receiving chamber;
   (b) an independent phalangeal body having a first end adapted for operative securement to human bone and a second end defining an axially oriented receiving chamber;
   (c) a hinge means joining said independent phalangeal body to said metacarpal body for twisting, flexing, pistoning, distracting, and laterally rotating said phalangeal body relative to said metacarpal body;
   wherein said first ends of said independent metacarpal and phalangeal bodies include a self-tapping threaded portion with a plurality of spaced interrupting channels; and
   wherein said second ends of said independent metacarpal and phalangeal bodies are conical in shape with smooth exterior surfaces.

2. A prosthesis device for phalangeal joint replacement between a proximal phalangeal or metacarpal bone and a distal phalangeal bone comprising:
   (a) an independent metacarpal body having a first end adapted for operative securement to human bone and a second end defining an axially oriented receiving chamber;
   (b) an independent phalangeal body having a first end adapted for operative securement to human bone and a second end defining an axially oriented receiving chamber;
   (c) a hinge means joining said independent phalangeal body to said metacarpal body for twisting, flexing, pistoning, distracting, and laterally rotating said phalangeal body relative to said metacarpal body;
   wherein said hinge means includes:
   (A) a hinge stem having a ball element at one end and an opposite extending end, wherein said extending end operatively engages said receiving chamber of said phalangeal body;
   (B) a hinge body having a first extending end which operatively engages said receiving chamber of said metacarpal body such that said metacarpal body may be engaged by said extending end, and having a second end defining a curvilinear exterior surface and an interior socket for receiving and holding said ball element of said hinge stem, allowing flexing and lateral rotation; and
   (C) a hinge retainer intermediate said first extending end and said ball element, said hinge retainer having a substantially concave undersurface dimensioned to extend over a predetermined portion of the exterior surface of said hinge receptacle of said hinge body and wherein the undersurface is complementarily contoured to the exterior surface thereof.

3. A prosthesis device as claimed in claim 2, wherein said socket of said hinge means includes enlarged or recessed portions with respect to said ball element, thereby allowing a predetermined amount of lateral rotational movement of said ball element adjacent said recessed or enlarged portions.

4. A prosthesis device as claimed in claim 3, wherein said hinge stem further comprising a neck between said ball element and said hinge retainer wherein said socket includes a radially located slot sized and positioned to allow movement of said neck through said slot and prevent said ball element of said hinge stem from moving out of said socket, and thereby allowing flexing.

5. A prosthesis device as claimed in claim 4, wherein said slot has a radial length sufficient to allow said hinge stem to pivot about a predetermined number of degrees around said hinge body, thereby allowing flexing.

6. A prosthesis device as claimed in claim 5, wherein said hinge retainer further comprising an opposite extending edge and wherein said phalangeal body further comprising a lip such that said opposite extending edge engages said lip and prevents rotation of said phalangeal body about said hinge body beyond a predetermined point.

7. A prosthesis device as claimed in claim 6, wherein said hinge body defines a flat surface allowing said metacarpal body to abut against said flat surface, while engaged by said extending end of said hinge body.

8. A prosthesis device as claimed in claim 7, wherein said phalangeal body and said metacarpal body are made of titanium.

9. A prosthesis device as claimed in claim 8, wherein said hinge stem is made of an alloy of cobalt and chrome.

10. A prosthesis device as claimed in claim 9, wherein said phalangeal body and metacarpal body are tapered and have self-tapping threads on their ends, said threading defining uniformly spaced interrupting channels.

11. A prosthesis device as claimed in claim 10, wherein said metacarpal body further defines a circular rim on its widest end which abuts against said flat surface of said hinge body.

12. A prosthesis device as claimed in claim 2, wherein said hinge body is made of plastic which may flex when said metacarpal body is distracted away from said extending end of said hinge body, thereby allowing energy absorption which might otherwise be transferred to the bones connected.

13. A prosthesis device as claimed in claim 1, wherein said hinge means comprising:
  (a) a hinge stem having a ball element at one end and having a bore transversely therethrough and an opposite extending end, wherein said extending end operatively engages said receiving chamber of said phalangeal body;
  (b) a hinge body having a first extending end which operatively engages said receiving chamber of said metacarpal body such that said metacarpal body may be engaged on said extending end, and having a second end defining a socket and adjoining a radial slot and a transverse slot of predetermined dimensions transversely defined through said hinge body, said socket sized to captively receive and retain therein said ball element of said hinge stem, allowing limited universal movement; and
  (c) a hinge pin dimensioned and sized to be received within said bore of said ball element and having a length sufficient to engage interior walls of said transverse slot through said socket when fitted within said bore, wherein said hinge pin securably retains said ball element within said socket and restricts relative movement of said ball element when said hinge pin engages said interior walls of said transverse slot.

14. A prosthesis device as claimed in claim 13, wherein said socket of said hinge body includes enlarged or recessed portions with respect to said ball element, thereby allowing a predetermined amount of lateral rotational movement of said ball element adjacent said enlarged or recessed portions, and wherein said interior walls of said transverse and radial slots outwardly taper at predetermined locations, thereby allowing said hinge pin and said ball element additional lateral rotational movement where the interior walls of said slots are outwardly tapered.

15. A prosthesis device as claimed in claim 14, wherein said hinge stem further includes a neck between said ball element and said opposite extending end wherein said socket includes a radially located slot sized and positioned to allow movement of said neck through said slot and prevent said ball element of said hinge stem from moving out of said socket, said radially located slot allowing for flexing movement of the prosthesis, and wherein said hinge stem includes a collar between said neck and said opposite extending end of said hinge stem, wherein said second end of said phalangeal body has at least one extending tab to engage said collar and prevent relative rotational motion between said collar and said phalangeal body.

16. A prosthesis device as claimed in claim 15, wherein said first extending end of said hinge body is tapered and defines a flat surface allowing said metacarpal body to abut against said flat surface, wherein said receiving chamber of said metacarpal body is dimensioned to receive said extending end of said hinge body so that said metacarpal body can seat or distract and flex when distracted while engaging said extending end of said hinge body.

17. A prosthesis device as claimed in claim 16, wherein said phalangeal body and said metacarpal body are made of titanium, wherein said hinge stem is made of an alloy of cobalt and chrome, and wherein said phalangeal body and said metacarpal body are tapered and have self-tapping threads on their ends, said threading defining uniformly spaced interrupting channels.

18. A prosthesis device as claimed in claim 1, wherein said second end of said metacarpal body and said second end of said phalangeal body including slots engagable by a tool for rotatively implanting said bodies in their respective bones.

19. A prosthesis device as claimed in claim 2, wherein said extending end of said hinge body is axially offset from said hinge stem when said hinge means is in a fully extended position, thereby offering greater mechanical advantage to the prosthesis device.

20. A prosthesis system for phalangeal joint replacement comprising:
  (a) a phalangeal body having a first end including a receiving chamber;
  (b) a metacarpal body having a first end including a receiving chamber;
  (c) a hinge member having a first stem and a second stem, wherein said metacarpal body operatively associates with said hinge member and said first end is adapted to receive said first stem and having a second extending end adapted to be operatively secured to a metacarpal or proximal phalangeal bone; said second stem of said hinge member being adapted for engagement with said receiving chamber of said phalangeal body, said phalangeal body having a second end for securement to a distal phalangeal bone, said hinge member having an intermediate means for interconnecting said first stem said second stem, said intermediate means allowing flexing, pistoning, and limited universal movement of said first stem and said second stem and limited radial and axial rotational movement relative to each other, wherein said second stem of said hinge member is conical and an end of said metacarpal body nearer said hinge member includes a self-tapping threaded segment on an exterior surface of said metacarpal body with a plurality of spaced interrupting channels oriented transversely to said threads and an opposite end of said metacarpal body being free of threads.

21. The prosthesis system in accordance with claim 20 wherein said intermediate means of said hinge member includes a ball portion loosely and captively received within a ball receptacle portion, whereby said flexing, limited universal movement and limited radial and axial rotational and deflecting movement is obtained.

22. A prosthesis system for phalangeal joint replacement comprising:
   (a) a metacarpal member having a first end including a tapered receiving chamber with outwardly tapered interior walls;
   (b) a hinge body having a first stem and a second stem, wherein said first stem is adapted to be operatively secured to a phalangeal bone or the like; said second stem of said hinge member being adapted for engagement with said receiving chamber of said metacarpal body, said second stem of said hinge member having tapered exterior walls to compliment said interior walls of said tapered receiving chamber of said metacarpal body and allow said second stem to engage said receiving chamber and allow seating and distracting movement between said second stem and said tapered interior walls, thereby allowing an additional degree of flexing when distracted, said metacarpal body having a second end for securement to a proximal phalangeal or metacarpal bone, said hinge member having an intermediate means for interconnecting said first stem and said second extending stem, said intermediate means allowing flexing and limited universal movement of said first stem and said second extending stem and limited axial movement relative to each other;

wherein said second stem of said hinge member is conical and an exterior surface of an end of said metacarpal body nearer said hinge member includes a self-tapping threaded portion with a plurality of spaced interrupting channels oriented axially.

23. A prosthesis system for phalangeal joint replacement comprising:
   (a) a metacarpal body having a first end including a tapered receiving chamber with outwardly tapered interior walls;
   (b) a hinge member having a first stem and a second stem, wherein said first stem is adapted to be operatively secured to a phalangeal bone or the like; said second stem of said hinge member being adapted for engagement with said receiving chamber of said metacarpal body, said second stem of said hinge member having tapered exterior walls to compliment said interior walls of said tapered receiving chamber of said metacarpal body and allow said second stem to engage said receiving chamber and allow seating and distracting movement between said second stem and said tapered interior walls, thereby allowing an additional degree of flexing when distracted, said metacarpal body having a second end for securement to a proximal phalangeal or metacarpal bone, said hinge member having an intermediate means for interconnecting said first stem and said second extending stem, said intermediate means allowing flexing and limited universal movement of said first stem and said second extending stem and limited axial movement relative to each other;

wherein said second stem of said hinge member is unitary and formed of flexible plastic, whereby additional flexing movement is obtained.

* * * * *